United States Patent [19]
Moore

[11] Patent Number: 6,019,109
[45] Date of Patent: Feb. 1, 2000

[54] DENTAL FLOSSING TOOL AND METHOD

[76] Inventor: Timothy D. Moore, 37 E. 8th Ave., Columbus, Ohio 43201

[21] Appl. No.: 08/953,676

[22] Filed: Oct. 17, 1997

[51] Int. Cl.[7] ..................................................... A61C 15/00
[52] U.S. Cl. ............................................................. 132/323
[58] Field of Search .................................... 433/146, 147, 433/216; 132/323, 324, 326; 84/422.4

[56] References Cited

U.S. PATENT DOCUMENTS

| | | | |
|---|---|---|---|
| 3,799,177 | 3/1974 | Bragg | 132/326 |
| 3,831,611 | 8/1974 | Hendricks | 132/324 |
| 4,162,687 | 7/1979 | Lorch | 132/323 |
| 4,202,241 | 5/1980 | Lucas | 84/422.4 |
| 4,342,324 | 8/1982 | Sanderson | 132/324 |
| 4,403,625 | 9/1983 | Sanders et al. | 132/323 |
| 4,657,034 | 4/1987 | Koski | 132/324 |
| 4,926,820 | 5/1990 | Wearn | 132/323 |
| 5,224,501 | 7/1993 | McKenzie | 132/323 |
| 5,406,965 | 4/1995 | Levine | 132/323 |
| 5,564,446 | 10/1996 | Wiltshire | 132/323 |
| 5,570,710 | 11/1996 | Wei et al. | 132/323 |
| 5,692,532 | 12/1997 | Gabrousek | 132/323 |

FOREIGN PATENT DOCUMENTS

| | | | |
|---|---|---|---|
| 2 183 485 | 6/1987 | United Kingdom | 132/323 |

Primary Examiner—Ralph A. Lewis

[57] ABSTRACT

A dental flossing tool and method for flossing of the teeth using that tool is provided. The tool includes two elongated, rod-shaped handle elements and a length of dental floss that is removably secured at its opposite ends to respective ones of the handle elements at their terminal ends. Each handle element is provided with a bulb at the terminal end to which the floss is attached with the bulbs being larger in transverse cross-section relative to the longitudinal axis of its handle element than is the adjacent portion of the handle element. This results in a depressed annular region in which floss is wound and functions to retain the floss on a handle element. Each handle element includes a hand-grip section disposed in remote relationship to the terminal end provided with a bulb enabling a user to grip the element in a respective hand for support thereof and independent manipulation in effecting a flossing operation. The user holds the handle elements in separated relationship to maintain the floss extending between the terminal ends taut as an operative flossing section while inserting it between a pair of adjacent teeth and moving it to effect removal of debris. At intermittent intervals the user revolves the handle elements to concurrently unreel a length of floss from one and reel a length onto the other thereby placing an unused section of floss in an operative position and placing the previously used section on a handle element for storage until being discarded upon termination of a flossing operation.

8 Claims, 3 Drawing Sheets

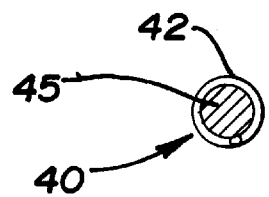
_Fig. 7_
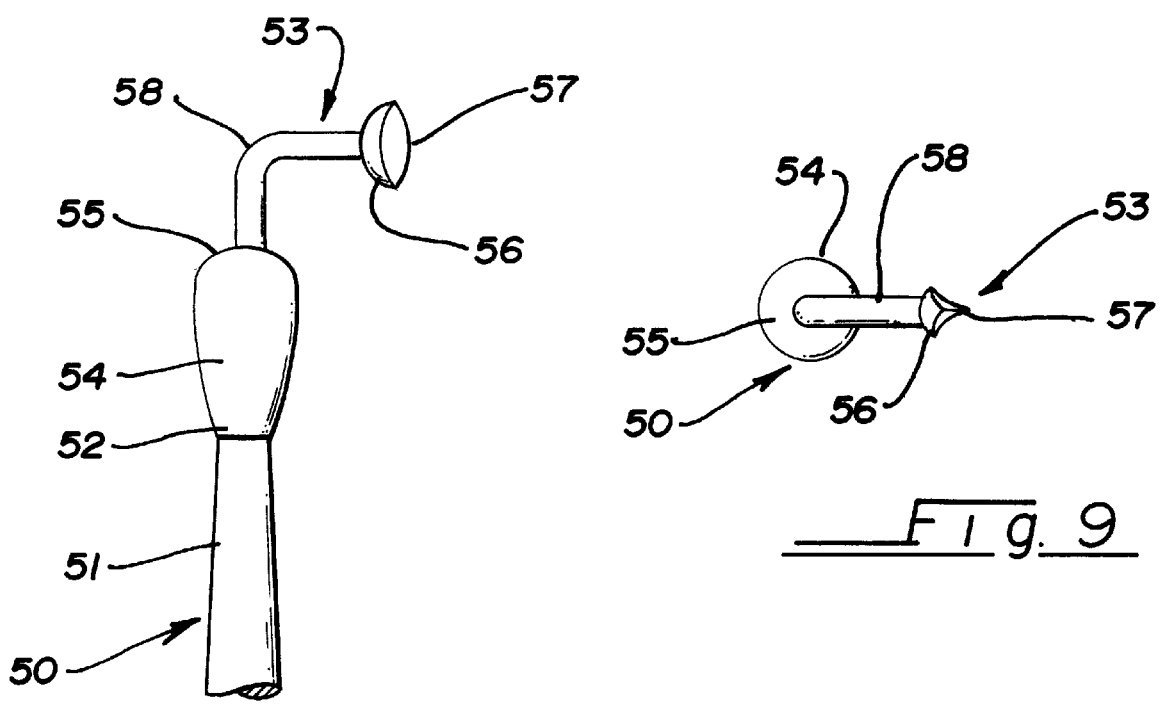
_Fig. 8_
_Fig. 9_

DENTAL FLOSSING TOOL AND METHOD

FIELD OF THE INVENTION

This invention relates generally to dental hygiene. It relates, in particular, to a tool and its method of utilization which significantly enhances cleaning of a persons teeth through use of dental floss. The tool comprises a pair of elongated, relatively slender handle elements that are each adapted to be gripped and independently manipulated by a respective hand of a person to cooperatively hold a length of dental floss tautly therebetween adjacent their terminal ends.

BACKGROUND OF THE INVENTION

It has become a common practice to utilize dental floss as a part of dental hygiene practice in addition to utilizing the customary tooth brush and dentifrice. This has become a desirable procedure for daily personal dental hygienic care to better assure removal of food particles from the teeth and, in particular, from the interstices between adjacent teeth. As is well known, utilization of only a customary tooth brush fails to effect the desired thorough cleaning of the interstices between adjacent teeth.

A common technique for utilization of dental floss is to take a length of floss from a floss dispensing container, wrap a portion of each opposite marginal end portion around an index finger of each respective hand and hold the end of the floss tightly against a finger by means of the associated thumb. With the fingers then separated to hold the interposed portion of the floss taut, the fngers and associated thumb are manipulated to displace the taut portion of the floss in a reciprocating manner through the interstitial space between any pair of adjacent teeth. The objective of this movement of the floss is to dislodge food particles caught or wedged between the teeth and thereby displace them to a position where they may be removed when rinsing the mouth. This technique is awkward due to the bulk of the finger and thumb that must be inserted in the mouth. It is a particularly awkward technique with respect to the teeth located at back of the mouth. Also, it is difficult to grip the floss around the ends of the fingers.

Attempts have been made to devise apparatus which will facilitate the flossing operation. Prior apparatus includes a number of different mechanical devices designed to hold a length of floss tautly between a pair of spaced apart supporting elements carried by a handle structure enabling manual manipulation to effect flossing of a persons teeth. Many of these prior art devices comprise mechanically complex structures incorporating numerous components requiring the user to have a significant amount of manual dexterity. A further major disadvantage of many of these prior art devices is that they are relatively costly. Many of these prior art devices are designed to incrementally advance the floss by manually operated or electric motor driven mechanisms to position an unused,clean section of floss in an operative position at periodic intervals. These mechanically or electrically operated devices are prone to break thereby requiring difficult and costly repair. Additionally, these mechanically or electrically operated devices add bulk and weight to such flossing devices rendering them more difficult to hold and manipulate.

Three examples of prior art devices shown in previously issued U.S. patents are hereinafter specifically identified and their structures briefly described to provide a background relationship to the present invention. These prior art devices differ in major respects from the physical structure of the flossing tool of this invention as well as in their respective modes of operation. Only one aspect of the physical structure of these three prior art devices is noted as having any degree of similitude to that of the flossing tool which is the subject of this disclosure and the appended claims. This aspect is that each of the tools includes a pair of elongated handle elements for support of a length of dental floss in a position where it can be effective in performance of a flossing operation. This single aspect of physical similitude is not anticipatory of the present inventive tool nor would it have made this tool or its mode of operation obvious to one having ordinary skill in this art. The three prior art patents noted herein and briefly discussed to clearly demonstrate their distinguishing structural features with respect to the present invention are listed as follows:

U.S. Pat. No. 5,469,874 issued Nov. 28, 1995 to Stuart L. Meyer, et al.;

U.S. Pat. No. 5,406,965 issued Apr. 18, 1995 to Steven K. Levine; and

U.S. Pat. No. 3,799,177 issued Mar. 26, 1974 to Kenneth R. Bragg.

Considering first the Meyer '874 patent, it will be readily noted that its physical structure comprises a pair of elongated rods that support a length of dental floss in the form of one or more loops.

These rods function as handles that are held by the user to manipulate the apparatus in performing flossing operations. A majority of the embodiments illustrated in this patent are formed with a plurality of small apertures in each of the handles in longitudinally spaced relationship but aligned transversely as between the pair of handles. The dental floss is threaded through opposed sets of apertures thereby forming loops that interconnect the handles at longitudinally spaced intervals. Threading of the floss through the apertures is not only a time consuming task but challenges a persons manual dexterity since the apertures are of a relatively small size. Furthermore, the threading operation is made even more difficult since the terminal end of the floss is in a frayed condition and it is well known that it is difficult to push a string having a frayed end through a small hole.

Two other embodiments of the apparatus shown in the Meyer patent do not have apertures through which the floss must be threaded as it is looped over the terminal ends of the handles. This requires the handles to be carefully held to avoid having the floss become disengaged.

A further disadvantage of the Meyer apparatus is the difficulty their structure presents to effect cleaning of the apparatus. They are designed to have the floss displaced at intermittent times during the course of a flossing operation thereby periodically presenting an unused length of floss at their operative terminal ends. Intermittent displacement of the floss is desirable as it advances a clean portion into a position where it effects the flossing operation. Concurrently, a portion of floss previously used and probably carrying debris, such as bits of food particles removed from the prior pair of teeth that had been flossed. This debris often becomes lodged in the apertures through which it passes, or is collected at edges of the handle structures about which the floss is trained, or is deposited on surfaces traversed by the floss. Regardless of the reason for debris becoming lodged on the handle components or structure, it is important that it be removed upon completion of a flossing operation to place the apparatus in a hygienically clean condition until again used in a tooth flossing operation.

Disclosed in Bragg's U.S. Pat. No. 3,799,177 are two embodiments of a flossing apparatus having a common structural feature of a pair of elongated elements that are supported with their respective terminal ends held in spaced apart relationship. A length of is supported between the opposed terminal ends and is used to effect a flossing function. It is threaded through tubular guides integrally formed with the elongated elements at their terminal ends. Again, as in the case of the Meyer et al. patent, their are the problems of threading the frayed end of the floss through a small aperture and effecting hygienic cleaning of the floss supporting elements at the conclusion of a flossing operation. Another significant problem with Bragg's apparatus is the difficulty encountered in manipulating the floss clamping mechanism provided to secure the floss to the elongated elements. It is manually operable to release the floss for incremental advancement of the floss to place a clean portion in operative flossing position.

The Levine U.S. Pat. No. 5,406,965, discloses an awkward flossing apparatus that has a single elongated rod-like, handle element for support of a length of floss in cooperation with the users finger and thumb. While the thumb and finger are inserted into the mouth, the handle element is held by the user's other hand in positioning the one terminal end adjacent the outwardly facing surfaces of the teeth. A length of floss is positioned in longitudinally extending, overlying relationship to the exterior surface of the handle element to which it is clamped by the fingers of the user's hand that is gripping the handle element. The floss extends to the terminal and is threaded through an aperture to be gripped by the user's thumb and finger whereby a short length of the floss is tautly held in a position where it can be effective in performing a flossing operation. Not only is the user faced with the difficult task of threading the floss through a small aperture in the handle element but is also faced with the difficult task of manipulating the cumbersome and bulky thumb and finger within the interior of the mouth.

SUMMARY OF THE INVENTION

A primary aspect of this invention is a dental flossing tool having a pair of slender, elongated handle elements designed to hold a length of dental floss between their respective terminal ends to be effective in performing a flossing operation. Each of the handle elements is adapted to be independently gripped by a respective hand of the user and independently manipulated in cooperative relationship in effecting displacement of the floss relative to the interstice between any selected pair of teeth that are to be cleaned. A length of floss is secured at each of its opposite ends to a respective handle element adjacent its respective terminal end. By appropriately manipulating the handle elements, the length of floss extending between the two handle elements is held taut to effect a flossing operation. Only the terminal end portions of the handle elements are placed in the mouth along with the floss leaving the remaining portions outside of the mouth where they may be readily gripped by the user's hands and freely manipulated independently. This enables the user to move the floss with convenience and ease to a desired position throughout the mouth to a selected pair of teeth and perform a floss-cleaning operation. In accordance with this aspect of the invention, the length of floss secured to the handle elements is greater than that which is required for effecting flossing of the space between a single pair of teeth. The additional length is initially wound around one of the handle elements adjacent its terminal end and is incrementally unwound with the portion previously used in a flossing operation being reeled up on the other handle element. This results in having a clean section of floss periodically placed in an operative position. To better assure the floss remains in close, adjacent position to a respective terminal end when reeled onto a handle element, the terminal end portion of each handle element is configured to form a circumferentially depressed axial region. This configuration is particularly beneficial as it assists in resisting the axially directed forces generated on the floss as it is displaced upwardly and downwardly through the usually small lateral space between any two adjacently disposed pair of teeth.

An advantageous embodiment of this invention is constructed with the terminal end portion of each handle element comprising two separable components. One component consists of a tapered end portion of the main part of a handle element with which it is integrally formed and terminates at a relatively small diameter. The other component is bulb-shaped having a terminal end surface which abuts against the end surface of the other handle component and is of the same diameter resulting in a smooth transition between adjacent surfaces. The bulb-shaped component is smooth surfaced, which in combination with its rounded extreme end, minimizes a likelihood of causing injury to a persons gums, lip, tongue or other parts of a person's mouth in the region of the teeth. Two separable components is advantageous as, when slightly separated, an end of the floss may be inserted therebetween and securely held by clamping when repositioned to place the abutting end surfaces in close, adjacent relationship.

Another embodiment of the invention has handle elements that are of a unitary construction including a hand-gripping portion of relatively long length terminating in a bulb-shaped end. The handle elements of this embodiment of the flossing tool are of essentially the same configuration as that of the first noted embodiment with the floss adapted to be wound about the tool at the intersection of the tapered section and the bulb-shaped end. The terminal end portion of the floss is placed axially along the tapered portion of the handle and is clamped thereto by the floss wound around the handle over the axially extending terminal end of the floss. Wrapping of the floss around the shaft avoids having any sharp edges of the handle elements come in contact with the floss which could inadvertently result in cutting of the floss. Another advantage of this embodiment of the flossing tool is the ease with which it can be cleaned by simple rinsing in the water flowing from a faucet. The previously described embodiment is also easy to clean in a similar manner.

The dental flossing tools of this invention are also advantageous in the case of persons who have teeth which are extremely closely spaced. While one may be able to push the floss downwardly between an adjacent pair of teeth so positioned, it may not be possible to pull the floss upwardly and out from the teeth without resulting in breakage of the floss. With the flossing tool of this invention, the bulb may be removed from one handle element permitting removal of the floss thus enabling the floss to be pulled latterally from between the teeth. It is then replaced on the handle element enabling flossing to continue.

These and other objects and advantages will become more apparent and better understood from the accompanying drawings and the following detailed description of those illustrative embodiments.

DESCRIPTION OF THE DRAWING FIGURES

FIG. 7 is a transverse sectional view taken along line 7—7 of FIG. 6.

FIG. 8 is a fragmentary plan view of a modified handle element having a removable bulb provided with a plaque scraper.

FIG. 9 is an axial end view of the tool shown in FIG. 8 as seen from the outer end of the scraper.

DESCRIPTION OF THE ILLUSTRATIVE EMBODIMENTS

Figure 1:
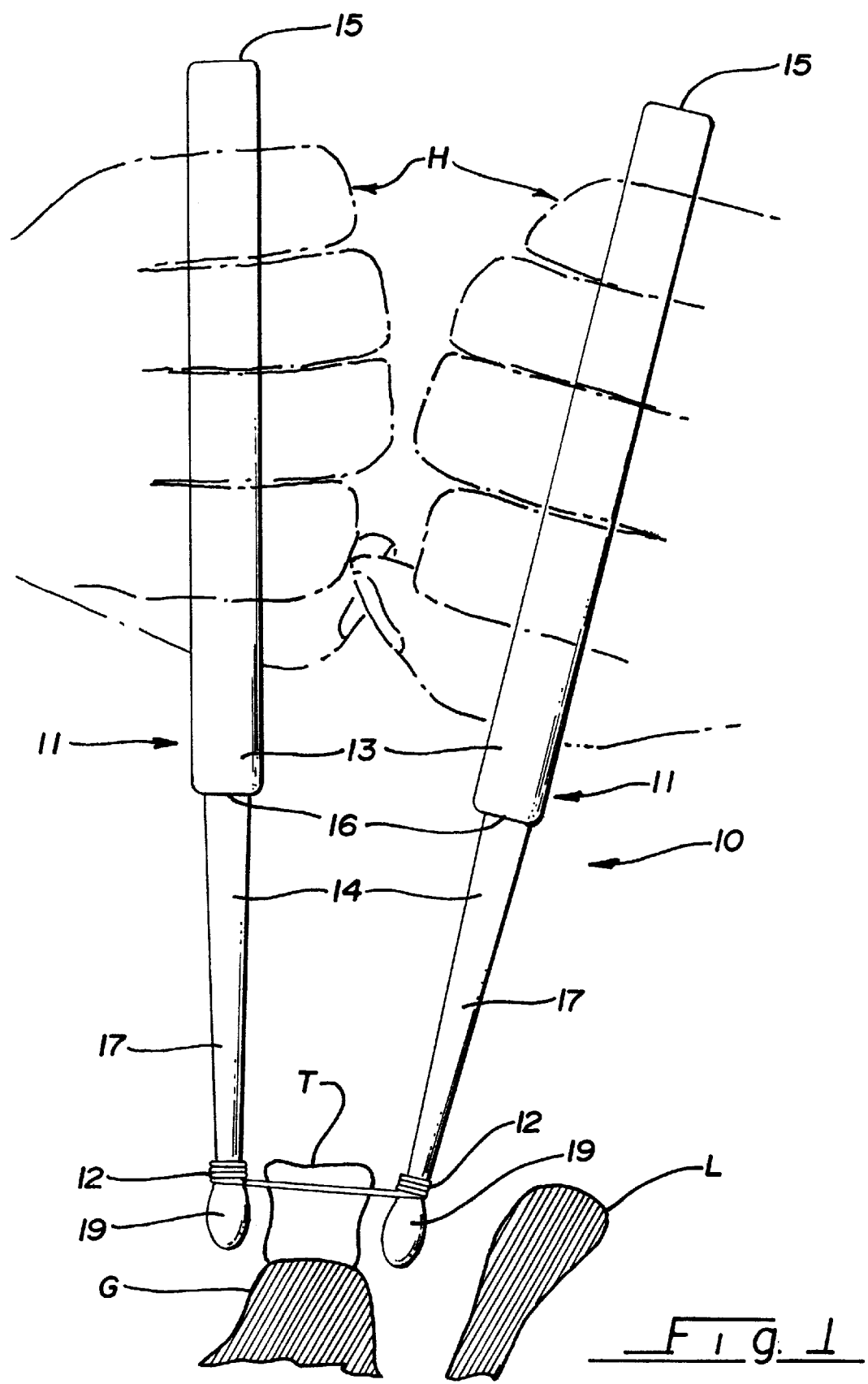
FIG. 1 is an elevational view of a flossing tool of this invention shown in operative relationship to a tooth.

A dental flossing tool 10 embodying this invention is shown in elevation in FIG. 1 disposed in operative position for performing flossing of a person's teeth as a part of the operation of cleaning the teeth in combination with a conventional tooth brush and dentifrice (not shown). For illustrating functioning of this flossing tool, it is shown in operative relationship to a tooth T as held in a supporting gum structure G. Also shown in association with the tooth and gum structure is a portion of a lower lip L with all of these three body components only being diagrammatically illustrated since they do not form a part of the invention. While it is the lower jaw with which this flossing tool is shown in functional operation, it will be recognized that a flossing function is effected in the same manner with respect to the upper jaw with this flossing tool.

The flossing tool 10 comprises two handle elements 11 and a length of dental floss 12. The handle elements are preferably of identical structure and configuration in a particular flossing tool being formed in accordance with one of the embodiments described herein and illustrated in the accompanying drawings. As can be seen in FIG. 1, the handle elements as shown in their entirety comprise relatively slender, elongated shafts having a hand-grip section 13 and a floss-holding section 14 that are integrally formed in axial alignment. These handle elements are each designed to be separately held by a respective hand of the user as shown by the diagrammatically illustrated hands H placed in encircling relationship about the hand-grip section of a handle element. A user may place the hand on the grip with the thumb extending in the illustrated direction or the hand may be positioned with the thumb extending in the opposite direction. Positioning of the hands is in accordance with the users preference and convenience in accomplishing efficient, effective performance in flossing of the teeth.

Referring to FIG. 1, an advantageous constructional configuration of a handle element 11 is of a total length of the order of 6½ inches with the hand-grip section 13 comprising 4 inches. It is shown as being of cylindrical shape having a diameter of the order of ⅜ inch and a terminal end surface 15 remote to the floss-holding section 14. These dimensions are considered typical for an average sized hand. A person with larger hands may prefer a tool having longer hand-grip sections and perhaps of larger diameter. These specific dimensions given for the hand-grip section, or for any other part of the handle are not to be considered limitative or in any manner restrictive of the scope of the invention. The hand-grip section terminates in remote relationship to the end surface 15 in an annular end surface 16 from which the floss-holding section axially extends. The floss-holding section includes a tapered section 17 of 2 inch length having a diameter of 0.235 inch at its coaxial juncture with the hand-grip section end surface 16. It diminishes in diameter to 0.150 inch at its end surface 18 and point of juncture with a terminal end bulb 19. The end bulb is 0.250 inch in length with a maximum diameter of 0.250 inch thus being essentially spherical in shape but having a terminal end surface 20 that is equal to the end surface 18 of the tapered section 17. This construction can be best seen in FIG. 2 with the bulb actually having an oblate shape since its length is slightly shorter than its diameter. This shape of the stated dimensions results in a configuration that fits conveniently in the mouth, particularly in the regions between the lip L and adjacent portions of the gum G with minimum likelihood of injury to the gum or to the lip during a flossing operation.

Figure 2:
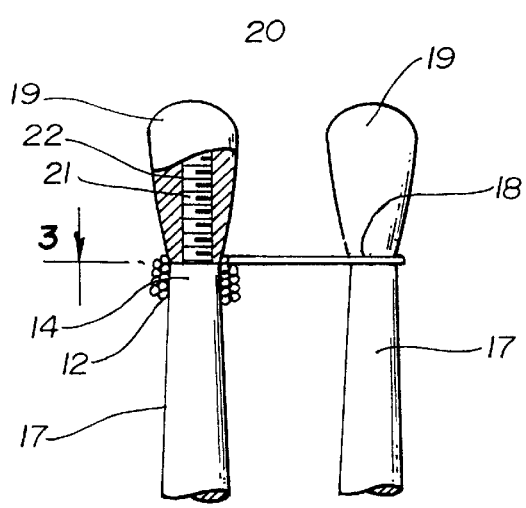
FIG. 2 is a fragmentary plan view on an enlarged scale of the operative end of the flossing tool shown in FIG. 1 with portions thereof broken away for clarity of illustration.

The floss-holding section 14 is constructed in two parts as can be seen by reference to FIG. 2. These two parts include the terminal end bulb 19 which is secured to the tapered section 17 by means enabling them to be disassembled and reassembled. In this embodiment that means comprises a screw-threaded stud 21 and a mating socket 22. The stud is integrally formed with the tapered section 17 and extends a distance coaxially outward from its end surface 18. The socket 22 formed in the terminal end bulb and enables the bulb to be screwed onto the stud to bring the bulb's end surface 20 closely adjacent to, or into contacting engagement with the tapered section's end surface 18.

A length of dental floss 12 is secured to each of the floss-holding sections 14 at the juncture of the respective bulb 19 and the end surface 18 of a tapered section 17 of a handle element 11. The handle elements are manipulated to hold the portion of dental floss extending therebetween taut as shown in FIG. 1 where it is operative to be inserted between a pair of adjacently disposed teeth T and be capable of effecting a flossing operation.

Figure 3:
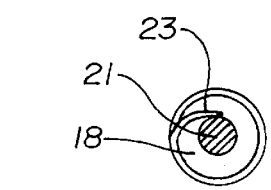
FIG. 3 is a fragmentary transverse sectional view taken along line 3—3 of FIG. 2.

Securing of the floss 12 to each of the respective handle elements 11 is best seen by reference to FIGS. 2 and 3. Each end bulb 19 is partially removed by unthreading it from its respective stud 21 leaving a space between the opposed end surfaces 18 and 20 which is sufficiently wide to admit the floss. A marginal end portion 23 of each end of the length of the floss is inserted in this space and trained around the stud as shown in FIG. 3. It is not necessary that this terminal end portion be overlapped where it overlies the end surface 18 although it may in accordance with the user's preference in executing the attachment operation. Winding of the floss around the stud is terminated at some point with the floss being brought out of the space between the opposed end surfaces 18 and 20 but using a finger to assure that the end portion of the floss wound around the stud remains within the space. At this point the bulb is threaded back onto the stud bringing the opposed end surfaces toward each other and ultimately clamping the floss therebetween. In those instances where the floss overlaps itself, the axially directed forces will compress the overlapped sections into each other to an extent in accordance with the characteristic of the particular floss being used. This same procedure is followed with respect to both handle elements.

Once the marginal end portion 23 at each end of the length of the floss is secured to a respective handle element 11 in accordance with the foregoing described procedure, the length of floss in excess of that required to perform a flossing operation is reeled onto one of the handle elements. The particular handle element selected for this initial reeling operation is dependent on the user's preference. It may be the element which is positioned to reciprocated adjacent the outer side of the teeth and next to the lip L as shown in FIG. 1. The portion reeled onto that element is maintained in the vicinity of the juncture of the bulb 19 and the tapered section 17 of the floss holding section 14 as can be best seen in FIG. 2. The floss has a tendency to form in multiple layers that extend short distances axially over the tapered section 17 and the bulb 19. It is preferable the length of floss used be kept at the minimum necessary for performance of a complete flossing operation, not only for reasons of economy, but to minimize the diametrical build up of the floss on any particular one of the handle elements. The diametrical build up must be limited to a diameter that is less than the maximum transverse dimension, or diameter of the end bulb 19. This is necessary to better assure that the floss will not be pulled axially over the bulb and off of the bulb when the handle element 11 is pulled upwardly with reference to FIG. 1 when removing the floss from between an adjacent pair of teeth during the course of a flossing operation. When greater lengths of floss are desired, more floss can be reeled onto the tapered section 17.

A flossing operation is initiated by the user gripping the handle elements 11 by means of positioning each of the hands on a respective one of the hand grip sections 13 and securely holding the handle elements. The handle elements are then independently manipulated to any selected one of appropriate positions for the particular pair of teeth being flossed, by way of example, such as is shown in FIG. 1. Concurrently, the user manipulates the handle elements in a manner to effect separating of their respective ends and continually stretch the length of floss 12 tautly therebetween. When thus positioned, the handle elements are then projected into the mouth bringing the taut length of floss into a position at the top of a pair of adjacently disposed pair of teeth, only one tooth T being shown, in parallel relationship to the interstice between those teeth. At that point the handle elements are projected downwardly pushing the floss between the teeth and down to the gum G. Thereafter, the handle elements may be manipulated to reciprocate the floss against the side surfaces of a tooth or between the inner and outer surfaces of the teeth, or a combination of both directions of motion. This movement and manipulation can also be performed as the floss is pushed downwardly between the teeth as well as when pulled upwardly. A user is enabled to do so since the handle elements are separately and independently manipulated. If deemed necessary, this operation may be repeated. It will be noted that only smooth surfaces of handle elements are placed, or can be placed, in contact with the gum and lip tissues thereby minimizing the likelihood of irritation or injury.

Movement of the handle elements 11 is not limited to an apparently parallel reciprocation as is shown in FIG. 1. This is an exemplary illustration to demonstrate typical operation in effecting the flossing operation as it would likely occur at the front of a persons mouth. When moving around the arch of the jaw, such as toward the teeth at the rear of the mouth, it is likely that the user will position the handle elements at various positions found to be most convenient and efficient at any specific pair of teeth. For example, the user may keep the handle element at the exterior side of the teeth in a more perpendicular position while moving the handle element operating at the interior side to a more horizontal position to accommodate the physical constraints imposed by the upper arch of the mouth's interior. The handle element operating at the exterior side of the teeth may also be placed in a more horizontal position as one approaches the rear teeth due to the size of the mouth opening and the flexibility of the lips of a particular user. Also, the handle elements may be relatively manipulated to any number of varied positions such as bringing the respective terminal ends 15 closer together than the ends provided with the bulbs 19 and at which ends the floss 12 interconnects the handle elements. It is even possible that a user of this flossing tool would find it advantageous to cross the handle elements over each other at some point intermediate their opposite ends. Positioning of the handle elements with respect to the upper teeth is determined by similar conditions unique to the upper teeth.

As a result of performing a flossing operation, the floss 12 extending between the two handle elements 11 will engage with and tend to retain the food particles and other particles of debris removed from between a particular pair of teeth. It is desirable to utilize a clean section of floss between each pair of teeth, or every other pair of teeth, depending on the amount of debris accumulated on the floss at any particular time during the course of a flossing operation. Providing of a clean section of floss at any time is readily accomplished with this flossinq tool 10. When floss cleaning of the interstice between a specific pair of teeth is completed and it is desired to place a clean, new section of floss in operating position, this is quickly and easily accomplished with this flossing tool. After moving the handle elements to a position where the previously used section of floss is removed from the teeth, the user revolves the handle elements to unreal a length of floss that has not been used from the one handle element and reels the previously used section of floss onto the other handle element. This is shown in FIG. 2 as at the initial stages of a flossing operation. A majority of the floss which is unused is wound on the element at left side of with a small portion of the floss, the used portion carrying debris, having been wound on the element at the right side of that drawing figure.

When effecting a floss transfer operation, it is preferable to have both handle elements disposed in a position where the movement of the floss can be observed. A suitable location would be outside of the mouth. This is desired to enable the user to determine when the used section of floss has been fully reeled onto the second handle element. It also enables the user to determine when an appropriate length of new, unused length floss has been positioned between the two handle elements. While performing the floss transferring operation, the handle elements are held sufficiently separated to maintain the length of floss extending therebetween taut preventing the floss wound on the respective handle elements from becoming loose and sliding over the adjacent bulb 19. Once the transfer operation has been completed placing the new and unused section of floss in an operative position between the handle elements, the user may then continue with the flossing operation. The floss transfer operation is repeated as often as is necessary to keep a clean section of floss in an operative position.

When flossing of the entire set of teeth has been completed, the user then removes the floss 12 from each of the handle elements 11. Removal is effected by first partially unthreading each of the terminal end bulbs 19 from its respective stud 21. This releases the terminal end 23 of the floss previously clamped between the opposed surface 18 of the tapered section 17 and the end surface of the bulb 19. Further unthreading of the bulbs from their respective studs enables removal of the bulbs and permits the floss to be pulled off the bulbs 19 and tapered sections 17 and discarded. Alternatively, with the bulbs partially unthreaded thereby releasing the terminal ends of the floss, the handle elements may simply be revolved to unreel the floss.

At this point the user can readily rinse the handle elements in water running from a faucet or employ any alternative cleaning technique. This is a particular advantage which this flossing tool has over prior art flossing tools. If des, dry the components and rethread the bulbs onto their respective studs 21 to avoid loss during storage of the flossing tool 10 until such time as it is again desired to be used.

The flossing tool 10 is preferably fabricated from a material that is highly resistant to rusting or other types of corrosion since it is utilized in a water environment. Material such as stainless steel is advantageous as it also exhibits sufficient structural strength. Certain plastic materials also may exhibit adequate strength and have the desired resistance to corrosion.

In the embodiment shown in FIG. 1, the flossing tool 10 has handle elements 11 wherein the hand-grip sections 13 are of a cylindrical configuration in cross-section. These hand-grip sections may be otherwise configured. For example, they may be square or hexagonal in cross-sectional configuration.

Figure 4:
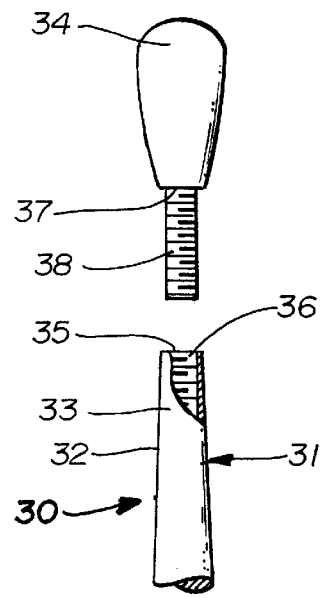
FIG. 4 is a fragmentary plan view of the operative end of a modified handle element with portions broken away for clarity of illustration but having the two components separated.

A portion of a handle element of a modified embodiment of the dental flossing tool is shown in FIG. 4. This flossing tool 30 is similar to that shown in FIG. 1 having a pair of handle elements 31 with only that portion of a handle element which differs in structure being shown. That portion consists of the terminal end of the tapered section 32 of a floss-holding portion 33 and a terminal end bulb 34 which are shown separated for clarity of illustration. The tapered section terminates in an end surface 35 disposed in transverse relationship to the longitudinal axis of the tapered section. Centrally formed in the marginal end portion of the tapered section is an axially extending socket 36 which opens at the end surface 35 and has an internal screw thread. The bulb 34 has an external surface configured similar to the bulb 19 of the FIG. 1 embodiment with an end surface 37 designed to abut the end surface 35 of the tapered section 32 and is of the diameter. A screw-threaded stud 38 integrally formed with the bulb projects a distance co-axially outward in perpendicular relationship to the bulb's end surface 37. The stud's screw thread mates with the internal thread of the socket 36 with the stud being of a length to enable the end surfaces 35 and 37 to be brought into contacting engagement, or at least sufficiently close proximity thereto to clamp a terminal end portion of a section of floss between those opposed end surfaces.

Functioning and operation of this FIG. 4 embodiment is essentially the same as the embodiment shown in FIGS. 1, 2 and 3. Each of the handle elements 31 functions to hold a length of floss (not shown) which is wound onto a respective element and can be held in taut relationship to effect a flossing operation. A terminal end portion of a length of floss is trained around the stud 38 that has been partially threaded into a respective socket 36 to an extent that leaves a small space between the opposed end surfaces 35 and 37 into which the terminal end portion of the floss may be inserted. With the floss inserted, trained around the stud and extending laterally to the exterior, the bulb 34 is turned to bring the opposed end surfaces into compressing engagement with the floss whereby it will be tightly held.

Figure 5:
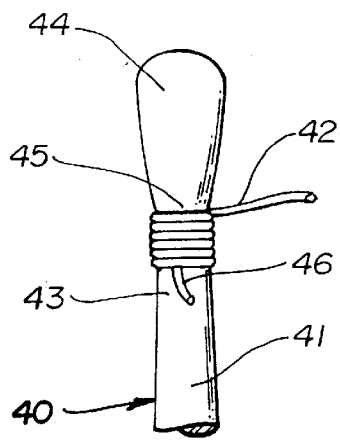
FIG. 5 is a fragmentary plan view of a terminal end portion of a modified hand element having a length of floss reeled thereupon in secured relationship.
Figure 6:
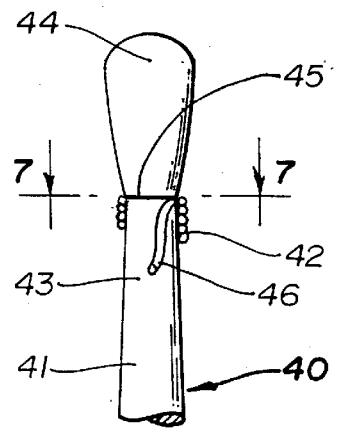
FIG. 6 is a fragmentary plan view of the modified hand element shown in of FIG. 5 with portions thereof broken away for clarity of illustration.

A third embodiment of a flossing tool 40 incorporating the structural concepts and operating principles of the previously described flossing tools and referenced to respective drawing figures is shown in FIGS. 5, 6 and 7 and described in the following paragraphs. This flossing tool 40 also comprises a pair of identical handle elements 41 that are each separately held by a respective hand of the user and are independently manipulated in displacing a length of dental floss in effecting performance of a flossing operation. A portion of only one handle element and a length of dental floss 42 is shown as the remainder of the handle element is the same as that of the first embodiment of the flossing tool 10 shown in FIG. 1. The difference in the tools resides in the end portion which carries the floss and is inserted in the mouth to place the length of floss in operative relationship to a pair of adjacently disposed teeth.

The handle elements 41 in this embodiment are of a unitary construction having an external surface configuration that is essentially the same as that of either of the other two embodiments when they have their respective bulbs 19, 34 positioned with their end surfaces in abutting engagement with the opposed end surface of the respective tapered section 17, 32. This third embodiment also has a floss carrying end as shown in FIGS. 5 and 6 having a tapered end section 43 and a terminal end bulb 44 which meet at a juncture point 45. The juncture point is of a diameter equivalent to that of the abutting end surfaces of the tapered sections and terminal end bulbs of the other two embodiments.

As previously indicated, the floss 42 is carried at this end of two handle elements 41 forming in combination therewith the flossing tool 40. Since only one handle element is shown, only a partial length of the floss extending between two handle elements with it being recognized that its total length is sufficient to enable appropriate spacing of the elements for effective flossing of the teeth. The total length of floss utilized for any one flossing operation is that determined necessary by a particular user for permitting incremental advancement of the floss to bring a clean and unused section into an operative position to enable flossing of the entire set of teeth.

In this embodiment the floss is retained on the handle elements 41 by always having a few turns of floss 42 wound on each tapered end section 43 at the their respective juncture 45. To better assure that the floss is retained in position during operation, it is advantageous that a short terminal end portion 46 of the floss at each of its ends be placed in axial alignment along each tapered end section 43 beginning at the respective juncture 45. This terminal end portion 46 of the floss is initially held in position by the users thumb or forefinger of one hand while a few turns of floss are tightly wound on the tapered end section by use of the other hand in overlying relationship to the end portion 46. This positioning and wrapping is shown in FIGS. 6 and 7. Winding of additional floss on the tapered end section 43 is accomplished either by continuing to hold the handle element 41 stationary in one hand while using the other hand to wrap additional floss around the end section or by rotating the handle element in reeling floss onto the end section from a supply that is fed through the thumb and fingers of the other hand. A similar reeling technique is employed with the other handle element's tapered end section although a lesser amount of floss is initially wound on that section. Regardless of the winding technique utilized, it is important to keep the floss taut as it is being reeled to assure that the floss which has been wound maintains a compressive force on the underlying windings. This keeps the floss from slipping around the tapered end section thereby enabling the user to maintain the operative section extending to the other handle element in a taut condition for optimum performance of the flossing operation.

A flossing operation is performed with the flossing tool 40 in essentially the same manner as described with respect to the tool 10 shown in FIG. 1. However, after completing flossing of the entire set of teeth, the remaining floss on each of the tapered sections 43 is completely removed by unreeling the remaining floss so that the terminal end portions 46 are released. The floss is then discarded. Thereafter the handle elements 41 are cleaned by rinsing in water, or by other cleaning techniques, and dried for storage.

Utility of this flossing tool is enhanced through capababilty of a handle element being modified to specifically function in removal of plaque which may form on tooth surfaces regardless of the diligence displayed by one in performance of brushing and flossing operations. An exemplary form of this modification is shown in FIGS. 8 and 9. This tool 50 comprises a handle element having a hand-grip section (not shown) similar to those of the FIG. 1 embodiment and an axially aligned tapered section 51 terminating in a small diameter, transverse end face 52. A plaque scraping element 53 is removably attached to the tapered section in axially outwardly extending relationship.

The plaque scraping element includes a bulbular base body 54 having an end face 55 which is adapted to abut the end face 52 of the tapered section 51. Mechanical interconnection of the two is effected by mating screw-threaded socket and stud that are each integrally formed with a respective one of the tapered section 51 and the base body 54 with each of those components being shown in broken lines in FIG. 8. It is advantageous that the socket be formed in the tapered section in axially extending relationship opening at its axial end face 52 and the stud be integrally formed with the bulbular base body 54 and extending perpendicularly outward from its end face 55. Integrally formed with the base body is a plaque scraping device 56 having a scraping blade 57 supported in axially outward relationship by an L-shaped arm 58. This illustrative blade has an operative edge 59 that is of a configuration which is effective for working on certain surfaces of certain teeth. This illustrated plaque scraping element 53 is to be considered typical as the active scraping blade may be various configurations which are of shapes designed for optimum functioning with particular teeth and tooth surfaces. A set of different devices could be provided with a particular flossing tool 10 of this invention giving the user great versatility.

From the foregoing description of the embodiments of the flossing tool and the accompanying drawings along with the description of a method of performing a flossing operation, it will be readily apparent that a significant improvement has been made in a tool for flossing of teeth. The two handle elements are of a configuration that efficiently holds an appropriate length of floss by means which permits the user at intermittent intervals during flossing of the entire set of teeth to displace the length of floss and position a clean and unused portion of floss between the terminal ends of the two laterally separated ends in an operative flossing position. Each of the handle elements is held by a respective hand whereby it may be independently manipulated to a position which is most convenient for placement in the mouth and tautly holding a short section of floss in proper location to effect flossing any selected pair of adjacently disposed teeth. The handle elements hold the floss at their operative ends in reeled relationship enabling the user to conveniently incrementally advance the floss by the simple technique of separately revolving each of the handle elements. By holding the handle elements in proper relationship, the user is able to maintain the reeled portions of the floss tightly wound and the operative section of the floss taut for effecting a highly efficient flossing operation but easily advance the floss through simple cooperative revolving of the handle elements. Mounting of a length of floss is expeditiously accomplished and cleaning is subsequently easily performed for purposes of hygienic sanitation.

Having thus described this invention, what I claim is:

1. A dental flossing tool comprising:
   A) two elongated handle elements each having a hand grip section and a floss holding section disposed in end-to-end axial alignment with respect to each other and to the longitudinal axis of a respective handle element, said hand grip section being of a length and cross-sectional configuration adapted to be securely held in a respective one of the user's hands, said floss holding section being of a predetermined length terminating at an operative end in remote relationship to said hand grip section and having a bulb at the extreme end of said operative end, said bulb being relatively larger in transverse dimension than that portion of the floss holding section immediately adjacent said bulb, said floss holding section being formed with a portion having a tapered configuration that is outwardly divergent from its juncture with said bulb toward said hand-grip section for at least a predetermined axial length thereby forming a depressed region of relatively short axial length immediately adjacent said bulb in which floss may be reeled; and
   B) a length of dental floss having opposed terminal end portions that are each secured to a respective handle element at said depressed region, said length of dental floss being of a length greater than that spacing desired at the operative ends of said floss holding sections when effecting a flossing operation with the excess portions of said floss adjacent each respective terminal end portion thereof adapted to be reeled upon the floss holding section in and adjacent the depressed region thereof to which it is secured whereby the separation of the operative ends of the floss holding sections is restricted and the intervening section of floss can be held taut through manipulation of the handle elements forming an operative section of floss and cooperative revolution of said handle elements about their respective longitudinal axes effects transverse displacement of floss from the floss holding section of one handle element to the floss holding section of the other handle element thereby enabling the user to replace a previously operative section of floss with a section of floss that has not been used but had been stored on the one handle element and reeling the previously operative section of floss onto the other handle element for storage while maintaining the operative section of floss taut.

2. A dental flossing tool according to claim 1 wherein said bulb is integrally formed with said floss holding section's tapered portion.

3. A dental flossing tool comprising:
   A) two elongated handle elements each having a hand grip section and a floss holding section disposed in end-to-end axial alignment with respect to each other and to the longitudinal axis of a respective handle element, said hand grip section being of a length and cross-sectional configuration adapted to be securely held in a respective one of the user's hands, said floss holding section being of a predetermined length terminating at an operative end in remote relationship to said hand grip section and having a bulb at the extreme end of said operative end, said bulb being relatively larger in transverse dimension than that portion of the floss holding section immediately adjacent said bulb, said floss holding section being formed with a portion having a tapered configuration that is outwardly divergent from its juncture with said bulb toward said hand-grip section for at least a predetermined axial length thereby forming a depressed region of relatively short axial length immediately adjacent said bulb in which floss may be reeled, and said bulb is separable from said floss holding section's tapered portion at their juncture to form an annular space therebetween for receiving therein a terminal end portion of said length of floss, and means for mechanically securing said bulb to said tapered portion and operable to clamp said floss's terminal end portion therebetween in secured engagement, said means being selectively operable to enable either clamped securing or release of said floss; and B) a length of dental floss having opposed terminal end portions that are each secured to a respective handle element at said depressed region, said length of dental floss being of a length greater than that spacing desired at the operative ends of said floss holding sections when effecting a flossing operation with the excess portions of said floss adjacent each respective terminal end portion thereof adapted to be reeled upon the floss holding section in and adjacent the depressed region thereof to which it is secured whereby the separation of the operative ends of the floss holding sections is restricted and the intervening section of floss can be held taut through manipulation of the handle elements forming an operative section of floss and cooperative revolution of said handle elements about their respective longitudinal axes effects transverse displacement of floss from the floss holding section of one handle element to the floss holding section of the other handle element thereby enabling the user to replace a previously operative section of floss with a section of floss that has not been used but had been stored on the one handle element and reeling the previously operative section of floss onto the other handle element for storage while maintaining the operative section of floss taut.

4. A dental flossing tool according to claim 3 wherein said means for securing of said bulb to said tapered portion includes a screw-threaded stud secured to one of said bulb and said tapered portion and extending a distance axially outward therefrom, and a screw-threaded socket formed in the other of said two components for mating engagement with said stud.

5. A dental flossing tool according to claim 4 wherein the terminal end of said floss is wrapped at least partially around said stud.

6. A dental flossing tool according to claim 4 wherein said terminal end of said floss is wrapped completely around said stud at least once to be disposed in overlapped relationship, said bulb and tapered portion being brought together by threading said stud into said socket to bring the opposed end surfaces of said bulb and tapered portion sufficiently close together to compress the overlapped portions of floss into tightly compressed engagement.

7. The method of flossing teeth by means of use of a dental flossing tool utilizing dental floss consisting of securing each of the opposite ends of a predetermined length of dental floss adjacent to a first end of a respective one of a pair of elongated, structurally rigid rod-form handle elements adjacent their first end, holding each of the handle elements in a respective one of the user's hands by gripping it at a hand-grip section formed with each respective one of the handle elements and disposed in axially remote relationship to its first end, revolving a first of the handle elements about its longitudinal axis to reel a substantial portion of said length of dental floss onto one of said handle elements leaving a relatively short length of floss extending between said handle elements that is sufficient to traverse a pair of adjacently disposed pair of teeth and forms an operative floss section, independently manipulating the handle elements to maintain the first ends of the handle elements separated to an extent that keeps the operative floss section extending therebetween taut to be capable of performing a flossing operation, maneuvering each of the handle elements in cooperative relationship to displace the operative section of floss between the selected pair of teeth as well as around their lateral sides to remove debris, progressively moving the operative floss section to other pairs of teeth by independent manipulation of the handle elements and to thereby effect flossing of the user's entire set of teeth.

8. The method of flossing teeth according to claim 7 including the step of changing the operative floss section at periodic intervals during flossing of a set of teeth to remove an operative floss section which has become excessively fouled with debris from use at an operative position and replace it with an unused section of floss by revolving each of the handle elements about its longitudinal axis to unreel an unused section of floss from the one handle element and reeling the used prior operative floss section onto the other handle element.

\* \* \* \* \*